United States Patent [19]

Angel

[11] Patent Number: 4,834,497
[45] Date of Patent: May 30, 1989

[54] FIBER OPTIC FLUID DETECTOR

[75] Inventor: S. Michael Angel, Livermore, Calif.

[73] Assignee: The United States of American as represented by the United States Department of Energy, Washington, D.C.

[21] Appl. No.: 19,841

[22] Filed: Feb. 27, 1987

[51] Int. Cl.⁴ .................................. G02B 6/16
[52] U.S. Cl. .................. 350/96.29; 350/96.15; 350/96.30
[58] Field of Search ............. 350/96.10, 96.15, 96.29, 350/96.30, 96.34; 250/227; 356/73.1, 432, 433, 435, 448

[56] References Cited

U.S. PATENT DOCUMENTS

| | | | |
|---|---|---|---|
| 4,050,895 | 9/1977 | Hardy et al. | 23/230 R |
| 4,270,049 | 5/1981 | Tanaka et al. | 250/227 |
| 4,367,040 | 1/1983 | Goto | 356/44 |
| 4,399,099 | 8/1983 | Buckles | 422/58 |
| 4,600,310 | 7/1986 | Cramp et al. | 356/432 |
| 4,634,856 | 1/1987 | Kirkham | 250/227 |
| 4,710,353 | 12/1987 | Tanaka et al. | 422/68 |

FOREIGN PATENT DOCUMENTS

| | | | |
|---|---|---|---|
| 3431997 | 3/1986 | Fed. Rep. of Germany | 350/96.29 |
| 57-106838 | 7/1982 | Japan. | |
| 60-166837 | 8/1985 | Japan. | |

Primary Examiner—William L. Sikes
Assistant Examiner—Frank González
Attorney, Agent, or Firm—Michael B. K. Lee; L. E. Carnahan; Judson R. Hightower

[57] ABSTRACT

Particular gases or liquids are detected with a fiber optic element (11, 11a to 11j) having a cladding or coating of a material (23, 23a to 23j) which absorbs the fluid or fluids and which exhibits a change of an optical property, such as index of refraction, light transmissiveness or fluoresence emission, for example, in response to absorption of the fluid. The fluid is sensed by directing light into the fiber optic element and detecting changes in the light, such as exit angle changes for example, that result from the changed optical property of the coating material. The fluid detector (24, 24a to 24j) may be used for such purposes as sensing toxic or explosive gases in the atmosphere, measuring ground water contamination or monitoring fluid flows in industrial processes, among other uses.

16 Claims, 4 Drawing Sheets

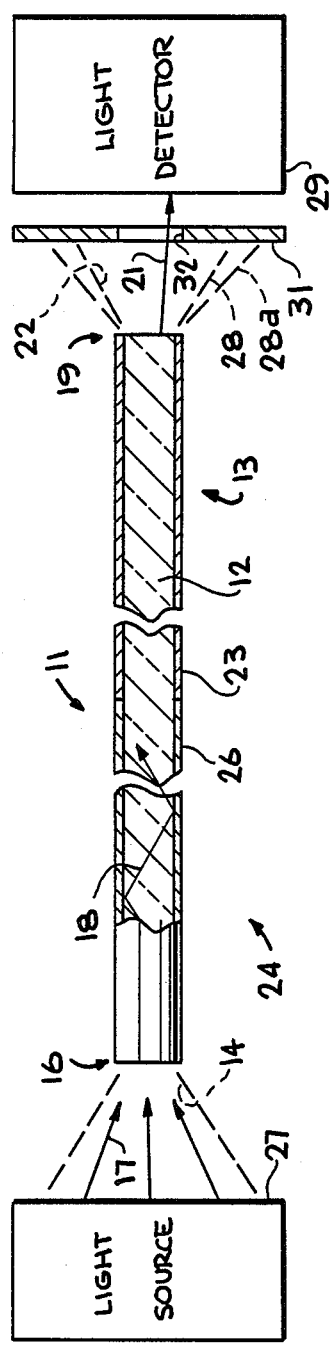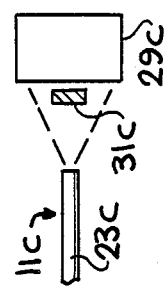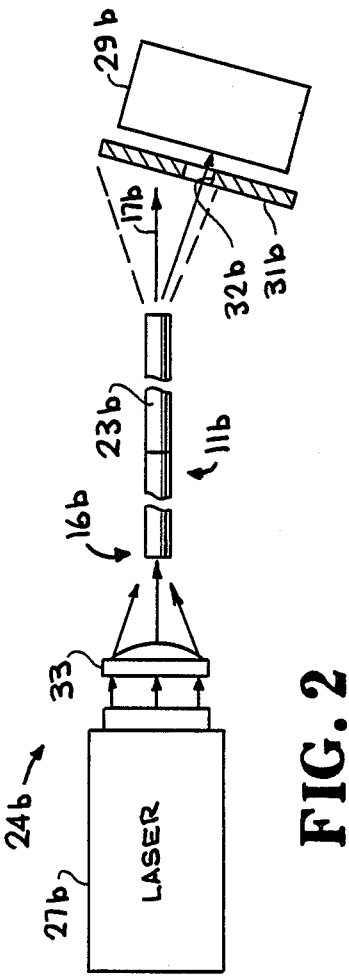
FIG. 1
FIG. 2
FIG. 3

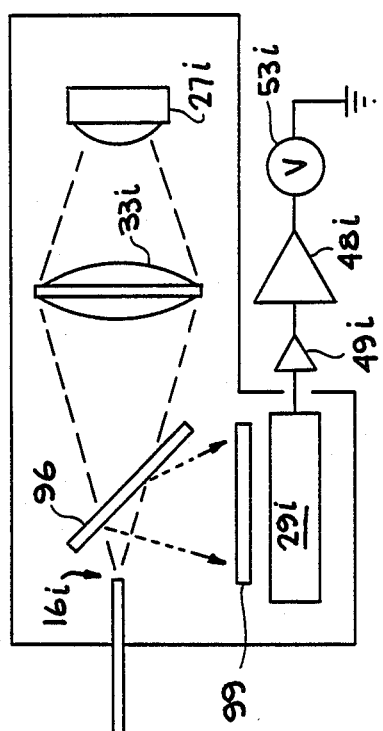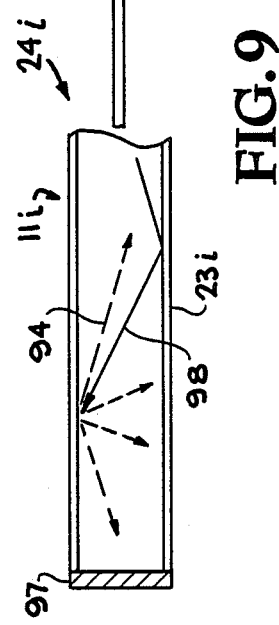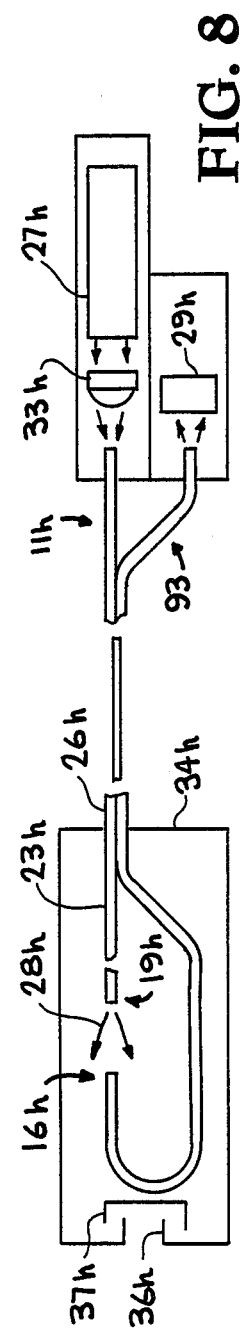
FIG. 9
FIG. 10
FIG. 8

FIBER OPTIC FLUID DETECTOR

The United States government has rights in this invention pursuant to Contract No. W-7405-ENG-48 between the United States Department of Energy and the University of California.

TECHNICAL FIELD

This invention relates to instruments for detecting the presence of a particular fluid or any of a group of fluids in an adjacent medium and more particularly to a detector which relies on optical effects within one or more fiber optic elements for the purpose of sensing fluids.

BACKGROUND OF THE INVENTION

Instruments for detecting specific gases or liquids in the adjacent environment have varied uses which include, among many others, the detection of toxic or explosive gases in the atmosphere, monitoring fluid flow constituents in industrial processes and detection of ground water contamination. There are many different known instruments for such purposes which variously respond to electrical, chemical or optical effects induced by the presence of the gas or liquid.

Many such instruments, for example, sense changes in electrical conductivity in a medium that result from the presence of the fluid. Others contain some substance that reacts chemically with the fluid to produce changes that are visible or otherwise detectable. Still others respond to changes of light conductivity or operate on the basis of X-ray, mass or optical spectrometry.

Each general type of fluid detector tends to have characteristics which make it suitable for some uses and inappropriate for others. Many are very costly and/or bulky and may require highly skilled operators. Some are inherently fragile and some are extremely sensitive to contamination. Detectors which depends on electrical effects to generate and/or transmit the desired data are prone to malfunction from electromagnetic interference. Detectors which require electrical conductors for signal transmission are also unsuitable for use in high voltage regions in the absence of substantial structural complications. Electronic detectors can also be hazardous if used for the detection of inflamable or explosive fluids because of the risk of ignition.

It would be advantageous if a fluid detector were available which can provide sensitive and reliable response while having a compact and inexpensive construction when that is desirable and which can be operated in diverse environments without complications. Such a detector should be immune to electromagnetic interference and should be capable of transmitting data over long distances without structural complication.

Insofar as I am aware, fiber optic technology has not been extensively used in gas or liquid detectors except possibly for transmitting data that has been generated by one of the conventional fluid detectors discussed above. One known technique which uses fiber optic elements in conjunction with the detection of gases relies on the fact that certain gases strongly absorb light of certain specific wavelengths. The presence of such gases in a region adjacent one end of a fiber optic element is sensed by directing light into the opposite end of the element and detecting variations of the intensity of the specific wavelengths after passage of the light through the region. The fiber optic element in such a system is essentially confined to the role of transmitting light to a detection site which is outside the fiber optic element. The apparatus does not operate on the basis of direct interaction between the detected fluid and the fiber itself.

The present invention is directed to overcoming one or more of the problems discussed above.

SUMMARY OF THE INVENTION

In one aspect of the present invention, apparatus for detecting a predetermined fluid or any of a predetermined group of fluids includes at least one fiber optic element having a light transmissive core and a coating on the core, a light source positioned to direct light into the fiber optic element for transmission along the element by repetitive internal reflections at the interface between the core and coating, and light detection means for detecting light which is emitted from the element. The fiber optic element is absorptive of the fluid or fluids which are to be detected. In particular, the coating along at least a portion of the core is a material which absorbs the fluid or fluids and which has an optical property that is changed by such absorption. The light detection means detects changes in a property of the emitted light that are caused by the changes of the optical property of the coating which occur in the presence of the fluid or fluids.

In one specific aspect of the invention, the coating material is one which exhibits a change of index of refraction upon absorption of the fluid or fluids which change alters the exit angle of light emitted from the element.

In another specific aspect of the invention, the coating material is one in which fluorescent light is produced in response to light from the light source and which exhibits a change in light transmissivity upon absorption of the fluid or fluids. The light detection means detects the fluoresent light.

In still another specific aspect of the invention, at least one additional fiber optic element is disposed against the coating material. The light detection means detects changes in light leakage into the additional fiber optic element that result from absorption of the fluid or fluids.

In still another aspect, the invention provides an instrument for detecting a specific fluid or any of a predetermined group of fluids which includes a light transmissive fiber optic element having a core with a coating on the side surface, the coating along at least a portion of the element being a material which absorbs the fluid or fluids and in which such absorption alters the optical properties of the material and thereby causes a change in the characteristics of light which propagates along the element. A light source directs the light into the fiber optic element and light detection means detect the changed characteristics in light which emerges from the element and produces an output signal indicative of the changes. The instrument also includes means for indicating detection of the fluid or fluids in response to the output signal.

Instruments embodying the invention may variously be constructed to signal the presence of a particular fluid or fluids at a detection region and/or to provide a quantitative reading of the concentration of fluid which has been absorbed from the adjacent medium. The instrument may, where appropriate, have an extremely simple, compact and inexpensive construction as fluids are sensed through effects which occur within a fiber optic element itself. The fiber optic element can, if necessary, transmit the desired data for long distances without additional components for the purpose. The fluid sensing and data transmission portions of the device are not subject to electromagentic interference, cannot ignite inflamable fluids and can be extended into high voltage regions without structural complications for the purpose.

BRIEF DESCRIPTION OF THE DRAWINGS

FIG. 1 is a schematic view of typical components of a fiber optic fluid detector embodying the invention.

FIG. 2 schematically illustrates a modification of the fiber optic fluid detector which is advantageous under certain conditions.

FIG. 3 depicts another modification of the fiber optic fluid detector which enhances sensitivity under certain conditions.

FIG. 8 is a schematic view of another fiber optic fluid detector with specialized adaptations for detecting fluid at a remote location.

FIG. 9 depicts an embodiment of the invention which detects fluids by utilizing a fluorescent coating in a fiber optic element.

FIG. 10 is a schematic view of still another embodiment of the fiber optic fluid detector which monitors fluids by sensing changes of light leakage between adjacent fiber optic elements.

DETAILED DESCRIPTION OF THE PREFERRED EMBODIMENTS

Figure 5:
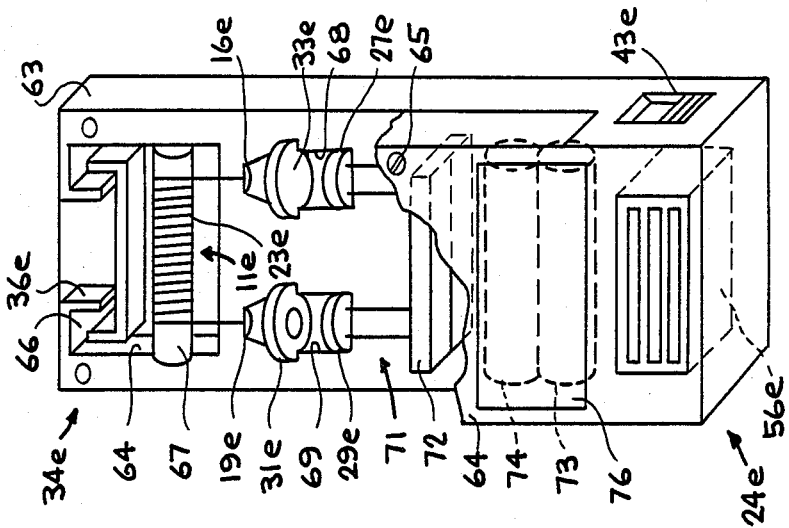
FIG. 5 is a broken out perspective view of a portable gas detector in accordance with still another embodiment of the invention.

Referring initially to FIG. 1 of the drawings, a basic component of the various embodiments of the invention is a fluid sensing fiber optic element 11 having a light transmissive core 12 formed of high index of refraction glass or similar material. The side surface of core 12 has a cladding or coating 13 of low index of refraction material. Such fiber optic elements 11 are in most cases very thin with diameters ranging down to 100 microns or less and thus are typically very lengthy in relation to their diameter.

As is understood within the art, fiber optic elements 11 exhibit an acceptance angle 14 determined primarily by the difference in the indices of refraction of the core 12, coating 13 and the external medium. Light which enters one end 16 of the fiber optic element 11 along ray paths 17 which lie within the acceptance angle 14 will propagate along the element by repetitive rotal interval reflections 18 at the interface between the core 12 and coating 13, although light directed strictly along the axis of a straight fiber optic may pass through without such reflections. Light which propagates along the fiber optic element 11 is emitted from the opposite end 19 along ray paths 21 which lie within an emergence angle 22. In a conventional fiber optic element, the emergence angle 22 is similar to the acceptance angle 14 but this is not necessarily the case in certain embodiments of the present invention as will hereinafter be discussed in more detail.

The cladding or coating 13 of a conventional fiber optic element may be glass or the like of low index of refraction and serves the purpose of protecting the interface at which total internal reflections 18 occur from external influences which could cause light loss. Thus the cladding material is conventionally one which is non-absorbent of fluids that might be present in the adjacent environment.

In contrast to the prior practice, at least a portion 23 of the coating 13 along the length of the present fiber optic element 11 is a material which absorbs the particular fluid or group of fluids that is to be detected. The coating material 23 is also one in which absorption of the fluid or fluids causes a change in an optical property of the material of a kind that is detectable by monitoring the light 21 that is emitted from the fiber optic element 11. The optical property of the coating 13 which is changed by such fluid absorption may, for example, be the index of refraction, light transmissivity or rate of fluorescent light emission depending on the particular coating material 23. Fiber optic fluid detectors 24 relying on each of these types of optical property change will be hereinafter described and components for detecting such changes by monitoring the light 21 emitted from the fiber optic element will also be described.

Sensitivity to the presence of the fluid depends in part on the length of fiber optic element 11 that is clad with the absorbent coating material 23. Thus in detectors 24 where the entire fiber optic element 11 can be situated in the region at which fluid is to be detected, it is usually advantageous that all or substantially all of the core 12 be clad with the absorbent coating material 23. In other detectors 24 it may be necessary that the fiber optic element 11 extend away from the fluid detection region in order to transmit output light 21 to a remote monitoring location or for other reasons. In such cases it is usually preferable that the portion of the element 11 which is outside the gas detection region be coated with conventional non-absorbent cladding 26.

The particular embodiment of the invention shown in FIG. 1 operates by sensing changes of index of refraction that occur in coating material 23 upon absorption of the fluid that is to be detected. Given a core 12 having a constant index of refraction, a lowering of the index of refraction of the coating material 23 results in widening of the emergence angle 22 and an increase in the index of refraction of the coating material reduces the emergence angle.

In order to detect the changes of index of refraction of coating material 23, a light source 27 is positioned to direct light into the input end 16 of fiber optic element 11. Light from source 27 which enters end 16 along ray paths 17 that are within the acceptance angle 14 then undergoes repeated total internal reflections 18 and is emitted at output end 19 as a spreading cone of light 28 having an apex angle conforming with the emergence angle 22.

For the reasons discussed above, the cone of light 28 becomes broader, as indicated at 28a, when fluid absorption lowers the index of refraction of coating material 23. This does not necessarily produce a significant change in the total light flux within the cone 28-28a but does result in a lower light intensity at any given area within the cone. A light detector 29 is positioned to monitor changes of light intensity at a limited portion of the light cone 28–28a and thereby detects the presence of fluid within the coating material 23.

Light detector 29 is spaced apart from output end 19 of the fiber optic element 11 and an opaque shield 31, having a light transmissive aperture 32, is disposed between the light detector and fiber optic element 11. Aperture 32 has a diameter smaller than the diameter of the light cone 28 at the region of the shield 31. This enables light detector 29 to respond to changes of light intensity or angular flux distribution within light cone 28–28a rather than to the total light flux in the cone which in many cases remains substantially constant. Shield 31 is not needed under all circumstances such as, for example, where the the light sensitive area of the detector 29 is small enough that it intercepts only a portion of the light within cone 28–28a. The shield 31 may also be dispensed with and light detector 29 may, if desired, be placed directly against the end 19 of the fiber optic element 11 if there is a gap at some intermediate location along the fiber optic light transmission path as will be hereinafter described in more detail in connection with another embodiment.

The specific fluid or group of fluids which is sensed by the fiber optic fluid detector 24 is dependent on the composition of the absorbent coating material 23. As one specific example, polystyrene plastic is impervious to most gases or liquids that are likely to be present in the environment of the detector 24 but is absorbent of long chain hydrocarbons, such as tuolene or nitro-benzene, that are present in liquid gasoline and gasoline vapor. Absorption of such hydrocarbon compounds lowers the index of refraction of the polystyrene. Thus a detector 24 having an absorbent coating 13 composed of or containing polystyrene can be used to sense leakage of gasoline from a container or pipeline either into the atmosphere or underground in the vicinity of buried storage tanks. Such a detector 24 may also be used to monitor changes in the concentration of gasoline vapor at particular locations within an oil refinery, service station or the like.

It should be recognized that absorbent coatings 23 of other compositions, typically polymeric materials, can be used to detect various other gases and/or liquids. In general, a coating material 23 may be used in detector 24 to sense the presence of a given fluid or any of a group of given fluids if it is absorbent of such fluid or fluids, exhibits a detectable change in an optical property in response to such absorption and is either non-absorptive of other fluids that may be present or does not undergo a change in the optical property upon absorption of such other fluids.

A light emitting diode is an advantageous light source 27 in many instances as it is compact and inexpensive although other light sources such as incandesent bulbs can also be used to provide light. Referring now to FIG. 2, it may be desirable under some circumstances to direct a greater amount of light into a fiber optic fluid detector 24b than is provided by light sources of the above described kind. Under such circumstances a laser 27b may be used to input light to the fiber optic fluid detector 24b. A focussing lens 33 may be disposed between the laser 27b and the input end 16b of the fiber optic element 11b to direct the laser output into end 16b. Use of the more intense light output of a laser 27b is particularly advantageous if the fiber optic element 11b is extremely long, as in some remote monitoring systems, as the intense light can be transmitted for longer distances without amplification.

Light which travels through the fiber optic element 11b along its axis or along ray paths 17b that are parallel to the axis is not affected by the absorbent coating material 23b and thus does not convey information on the possible presence of the fluid which is to be detected. Rather, to the extent that such light reaches the light detector 29b it dilutes the effect of light that does carry such information and thereby reduces sensitivity of the instruments. Light which travels through the fiber optic 11b at relatively small angles to the axis may have a similar effect as such light undergoes relatively few interactions with the coating material 23b. Sensitivity loss from these effects is minor and can be disregarded in many cases, particularly in instruments which use non-coherent light and long fiber optic elements. In such devices very little light passes through the fiber optic element without many interactions with the coating.

Under some circumstances the above described effect may not be minor and it may be preferable to shield the light detector 29b from light 17 which passes through the fiber optic 11b without substantial interaction with the absorbent coating 23b. This can be advantageous in fiber optic fluid detectors 24b having a laser 27b for a light source as a greater proportion of the light from such a source passes through the element 11b without interaction with coating 23b particularly if the element is linear. It can also be advantageous in instruments having a non-coherent light source if the fiber optic element 11b is too short to provide for repetitive interactions of substantially all transmitted light with the absorbent coating 23.

Shielding of the detector 29b from light which travels more or less directly through the fiber optic element 11b can be accomplished by placing the light detector 29b and apertured shield 31b, or alternately the light source, in an angled offset position relative to the axis of element 11b as shown in FIG. 2. Aperture 32b of shield 31b is preferably offset from the axis of element 11b by a distance at least equal to one half of the radius of the element.

Alternately, with reference to FIG. 3, the light detector 29c can be centered on the axis of fiber optic element 11c while being partially shielded by an opaque disc 31c provided that the light sensitive area of the detector 29c has a diameter greater than that of end 19c of the element. Disc 31c preferably has a diameter at least equal to that of end 19c and is centered on the axis of end 19c.

Figure 4:
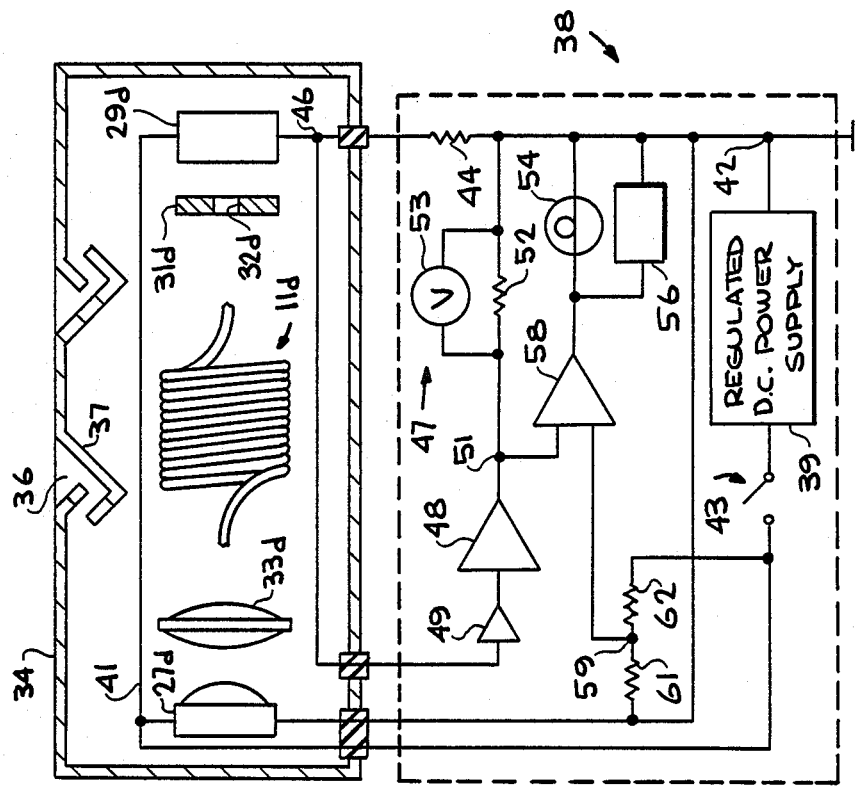
FIG. 4 is a partially schematic view showing structural components of another embodiment of the invention in greater detail and depicting an example of an electrical circuit suitable for indicating data.

As has been discussed above, efficiency of fluid detection is in part dependent on the length of the portion of the fiber optic element 11c which has absorbent coating material 23c. Referring now to FIG. 4, a desirably lengthy fiber optic element 11d can be arranged for sensing fluids in a limited area by convoluting the element, the element being formed into a coil in this example. In many cases it is preferable to shield the region of the element 11d, lens 33d, light source 27d, shield 31d and light detector 29d from external light by enclosing such components within an opaque housing 34. Housing 34 is provided with one or more fluid inlet openings 36 which are preferably spanned by light baffles 37. The inner surface of housing 34 and the surfaces of baffles 37 are preferably dark colored to enhance absorption of stray light.

In the embodiment of FIG. 4, the light source 27d is a light emitting diode and the light detector 29d is a photodiode of the known form which has a reverse current conductivity that varies in accordance with the variations in light flux which impinges on the photodiode. Suitable circuit means 38 for energizing such components and for indicating the presence of fluid which is to be detected may include a regulated direct current power supply 39 connected between B+ voltage conductor 41 and a chassis ground conductor 42 in series relationship with a control switch 43. Power supply 39 may be of one of the known forms which provide a constant output voltage.

Light emitting diode 27d is connected across conductors 41 and 42 and directs a constant light flux into fiber optic element 11d through a focussing lens 33d. Photodiode 29d is connected across conductors 41 and 42 in series relationship with a voltage dropping resistor 44. The light received by the photodiode 27d from element 11d increases in intensity when fluid is absorbed by the element. This reduces the internal resistance of the photodiode 27d. Consequently, the voltage at the circuit junction 46 between the phototdiode and resistor 44 rises in response to the presence of the fluid and by an amount which is dependent on the amount of fluid which is absorbed in element 11d.

Indicator means 47 for displaying data indicative of the rate of light reception at photodiode 29d or otherwise signalling the presence of fluid may take a variety of forms. In this example, an amplifier 48 has an input connected to circuit junction 46 through a preamplifier 49. The output terminal 51 of amplifier 48 is connected to chassis ground conductor 42 through a load resistor 52. A voltmeter 53, which may be of either the analog or digital form, is connected in parallel with resistor 52 and may be calibrated to display fluid concentration in appropriate units such as parts per million for example.

In some fluid detectors 24d it may only be necessary that the instrument visually and/or audibly signal the presence of fluid rather than providing a quantitative reading of fluid concentration. In such cases, an indicator lamp 54 and/or an audible signalling device 56 such as a buzzer, beeper or bell may be connected across conductors 41 and 42 in series with a normally open relay 57 of the solid state type in this example. Relay 57 is controlled by the output voltage from a comparator 58 which has one input connected to amplifier output terminal 51. The reference input of comparator 58 is connected to another circuit junction 59 between a pair of voltage divider resistors 61 and 62. Thus when the output voltage from amplifer 48 exceeds a reference voltage determined by the relative values of resistors 61 and 62, comparator 58 energizes relay 57 and thereby actuates the lamp 54 and audible signaling device 56. The fixed resistors 61 and 62 may be replaced with an adjustable potentiometer to enable manual selection of the fluid concentration that causes signaling by lamp 54 and device 56.

Structural details of fluid detectors 24d embodying the invention may take a variety of forms depending on the particular usage for which the instrument is designed. FIG. 5, for purposes of example, depicts a gas detector 24e which is portable and designed to be carried in a pocket or clipped to a persons garments.

Gas detector 24e has a rectangular housing 34e of opaque, electrically insulative material and includes a main body 63 and separable side cover 64 secured to the body by screws 65. A gas inlet opening 36e at the top of body 63 communicates with an interior chamber 64 through a convoluted light baffling passage 66. The fiber optic element 11e having gas absorbent coating material 23e is wound in coil form on a core member 67 which extends transversely in chamber 64.

The light input end 16e of element 11e extends from chamber 64 to one end of a light source chamber 68 within body 63. Light emitting diode 27e is disposed at the opposite end of chamber 68 and a focussing lens 33e situated at an intermediate location in chamber 68 directs light from the diode into end 163 of element 11e. The light emitting end 19e of element 11e extends into still another chamber 69 in body 63 which has the photodiode 29e at the opposite end and an apertured shield 31e extends across chamber 69 between the photodiode and end 19e. Electrical lead wires 71 of the light emitting diode 27e and photodiode 29e extend on to a circuit board 72 which is disposed transversely in body 63 below the diodes.

The lower portion of housing 34e is formed with a compartment 73 for receiving batteries 74 which supply current to circuit board 72 and side cover 64 is preferably provided with a disengagable wall member 76 for enabling access to the battery compartment without disassembly of the fluid detector 24e. An audible signaling device 56e is also disposed in the lower end of the housing 34e and the control switch 43e is situated at a sidewall of the housing. Circuit board 72 may have electrical components similar to those previously described for the purpose of energizing diodes 27e and 29e and for actuating the signaling device 56e in response to detection of gas.

Figure 6:
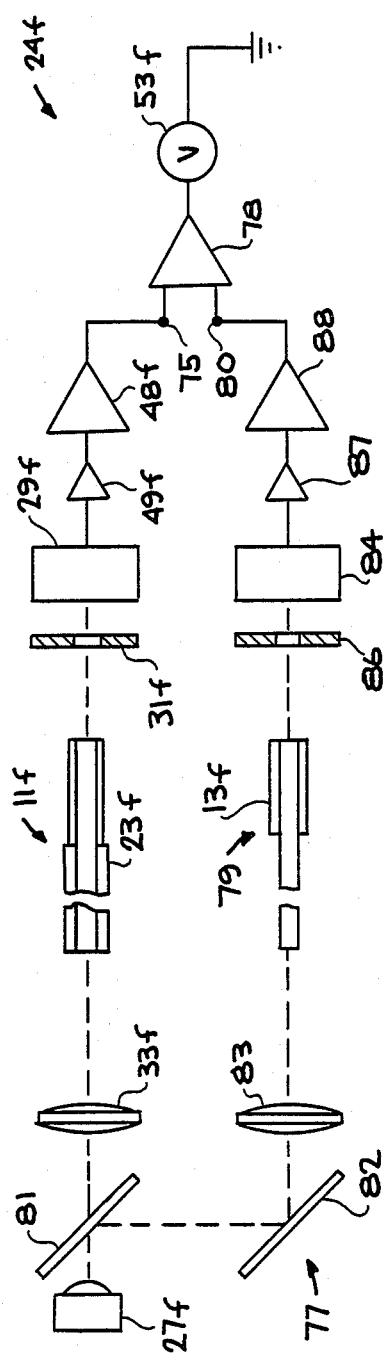
FIG. 6 is a schematic view of another fiber optic fluid detector having means for compensating for variable factors that can affect accuracy of response under some conditions.

The light sources 27 of the previously described embodiments of the invention emit light at a constant intensity so that variations in the amount of light sensed by the light detectors 29 will be accurately indicative of changes of fluid concentration in the absorbent coating 23 of the fiber optic elements 11. Variations in the light output of the light sources 27 due to malfunction, aging, drift of the voltage output of power supply 39 or other causes can detract from accuracy. Referring now to FIG. 6, compensating means 77 can be provided to maintain accuracy in the presence of light output variations at the light source 27f.

As in the previously described embodiments, the fluid detector 24f of FIG. 6 has a lens 33f focussing light from source 27f into one end of a fiber optic element 11f which has a coating 23f of the fluid absorbent material. A light detector 29f receives light emitted from the other end 19f of element lip through an apertured shield 31f. A preamplifier 49f and primary amplifier 48f transmit the output signal produced by light detector 29f to a voltmeter 53f for data readout in the manner previously described except that in this embodiment the primary amplifier is connected to the voltmeter through one input 75 of a ratio amplifier 78. The other input 80 of ratio amplifier 78 receives a voltage from the compensating means 77.

Compensating means 77 includes a reference fiber optic element 79 having dimensions similar to those of the fluid sensing fiber optic element 11f but which has a coating 13f of fluid impervious conventional cladding material such as low index of refraction glass. A beam splitter 81, such as a half silvered mirror, is positioned between light source 27f and lens 33f to direct one half of the output light of the source 27f to a parallel mirror 82 while the other half of the output light is focussed into the fluid sensing fiber optic element 11f through a lens 33f. Another similar lens 83 focusses the light intercepted by mirror 82 into the reference fiber optic element 79.

Light emitted from the reference fiber optic element 79 is detected by another light detector 84 through another apertured shield 86. Detector 84 and shield 86 are similar to detector 29f and shield 31f respectively and are spaced from element 79 by distances similar to the spacings of detector 29f and shield 31f from element 11f. The output signal of light detector 84 is transmitted to the second input 80 of ratio amplifier 78 by an additional preamplifier 87 and an additional primary amplifier 88.

Fluid detector 24f operates essentially in the manner hereinbefore described except that the signal voltage applied to voltmeter 53f is adjusted by the compensating means 77, to maintain accuracy, if the light output from source 27f should vary.

The voltage applied to ratio amplifier input 80 remains constant as long as the light output of source 27f remains constant since the non-absorbent reference fiber optic element 79 is not affected by the presence of the fluid that is to be detected. Under that condition, ratio amplifier 78 delivers a voltage to read-out voltmeter 53f that is proportional to the variable voltage at input 75, which indicates fluid concentration, divided by the constant voltage at input 80 and thus operation of the fluid detector 24f proceeds as previously described with reference to other embodiments. Any variation of the light output of source 27f results in an equal variation of the voltages at inputs 75 and 80 of ratio amplifier 78. This does not change the ratio of the voltage at inputs 75 and 80. Consequently the voltage applied to voltagemeter 53f does not change and remains accurately indicative of fluid concentration in absorbent coating 23f.

Compensating means 77 may be used to adjust for other environmental variables, in addition to the light variation, adjustment that can affect accuracy. Temperature variations,y for example, can influence the angular flux distribution of light emitted from the fiber optic element 11f. As such temperature changes affect both fiber optic elements 11f and 79, the voltages at ratio amplifier inputs 75 and 80 remain in the same ratio and the reading at voltmeter 53f continues to be accurately indicative of fluid concentration.

Figure 7:
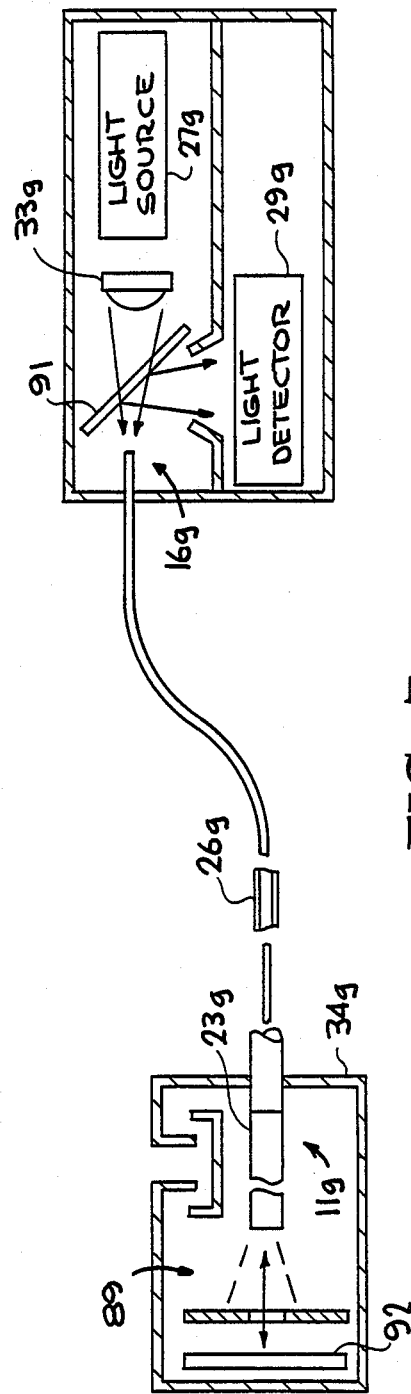
FIG. 7 is a schematic view of a fiber optic fluid detection system particularly adapted for monitoring fluids at a remote location.

Referring now to FIG. 7, the light source 27g and light detector 29g need not necessarily be at opposite ends of the fluid absorbent fiber optic element 11g and situating such components at the same end of the element can be highly advantageous for remote monitoring usages in which the fluid sensing components 89 are located a substantial distance away from the light source and light detector.

In the embodiment of FIG. 7, a focussing lens 33g again directs light from source 27g into an end 16g of a fiber optic element 11g. A beam splitter or half silvered mirror 91 is disposed between lens 33g and end 16g and is angled to direct one half of the light which emerges from end 16g to the light detector 29g. As mirror 91 is only partially light transmissive, only a portion of the light from source 27g reaches the fiber optic element 11g.

Fiber optic element 11g extends to an opaque housing 34g in which the fluid sensing components 89 are situated. At least the portion of fiber optic element 11g which is outside of housing 34g has non-absorbent conventional cladding 26g as it functions as a data conductor rather than as a fluid sensing element. At least a portion of the element 11g that is within housing 34g has the previously described fluid absorbent coating material 23g.

A mirror 92 is positioned in housing 34g, at right angles to the optical axis of end 19g of element 11g, to reflect a portion of the light which emerges from end 19g back into the fiber optic element 11g for transmission back to beam splitter 91 and thus to light detector 29g. An opaque shield 31g with central aperture 32g is disposed between fiber optic end 19g and mirror 92. The shield aperture 32g is smaller than the cone of light 28g which is emitted from end 19g. Thus mirror 92 receives and reflects back only a portion of the light which is emitted from element 11g and the amount of light which is reflected back varies in accordance with the variations of the amount of fluid absorbed in coating 23g. Light detector 29g monitors such variations in the reflected light and signals detection of the fluid in the manner hereinbefore described.

Shield 31g functions to prevent all light in cone 28g from being returned to the fiber optic end 19g in instances where the mirror is concave with a focal point at end 19g and is large enough to subtend the entire cone of light. The shield 31g may be eliminated in some instances such as where the mirror 92 is planar or has a diameter smaller than that of the cone of light 28g at the plane of the mirror. The mirror 92 does not return all light in cone 28 to end 19g under those conditions.

The embodiment depicted in FIG. 7 requires only a single fiber optic element 11g but there is a substantial loss of light intensity at beam splitter 91 both in the initial transmission of light to the fluid sensing components 89 and in the diversion of returned light to light detector 29g. Referring now to FIG. 8, another form of fluid detector 24h for remote monitoring operations avoids such signal intensity losses by using two fiber optic elements 11h and 93.

The first fiber optic element 11h receives output light from a source 27h through a focussing lens 33h and extends to an opaque housing 34h at the remote location where fluid is to be detected. Portions of the element 11h which are outside of housing 34h may be clad with conventional fluid impervious coating material 26h while at least a portion of the element that is within the housing is clad with the fluid absorbent coating material 23h.

The second fiber optic element 93 has a light input end 16h situated within housing 34h is spaced apart relationship with the light output end 19h of the fluid absorbent element 11h, the end 16h being located within the cone of light 28h which is emitted from end 19h and being oriented to receive a portion of such light for transmission back to a light detector 29h which may be near the light source 27h.

If fluid of the type to be detected enters housing 34h, through an opening 36h with light baffle 37h, the light cone 28h becomes narrower as a result of absorption of the fluid in coating material 23h. Consequently, more light enters end 16h of the return fiber optic element 93 and the increase of light intensity within element 93 is sensed by light detector 29h thereby indicating detection of the fluid. Shielding is not necessarily required between light detector 29h and the return fiber optic element 93 as the relatively small end 16h of the element intercepts only a portion of the cone 28h of light that emerges from the fluid absorbent fiber optic element 11h.

Referring again to FIG. 1, each of the embodiments which have been described up to this point operate on the basis of changes of index of refraction of the specialized coating material 23 that are induced by absorption of the fluid which is to be detected. The index of refraction changes cause detectable changes in the emergence angle 22 of light emitted from the fiber optic elements 11. It is also possible to sense fluids by detecting changes in other optical properties of the coating material 23 that result from absorption of fluid.

For example, with reference to FIG. 9, a fiber optic fluid detector 24i may respond to changes in the emission of fluorescent light 94 by a specialized coating material 23i that result from absorption of fluid.

In fluid detector 24i, a lens 33i again focusses light from a light source 27i into one end 16i of a fiber optic element 11i which has fluid absorbent coating material 23i in the region at which fluid is to be detected. A beam splitter mirror 95 is disposed between lens 33i and element 11i and is oriented to direct a portion of light that is emitted from end 16i to a light detector 29i. The output signal from light detector 29i may be transmitted to a readout voltmeter 53i by a preamplifier 48i and primary amplifier 48i.

The coating material 23i in this case is one which exhibits increased light transmissivity upon absorption of the fluid or fluids to be detected. It is also a material of a kind which fluoresces at a characteristic wavelength or combination of wavelengths in response to the light 98 from source 27i which propagates along the fiber optic element 11i. Polystyrene impregnated with any of various known fluorescent organic dyes, for example, is more or less opaque under most conditions but becomes more light transmissive upon absorption of long chain hydrocarbons such as are present in gasoline or gasoline vapor.

Fluorescent light 94 is emitted in all directions from the inner surface of coating 23i and thus a portion of such light is directed at angles which enable the fluorescence to propagate back along the fiber optic element 11i by repetitive total internal reflections. Beam splitter 96 then directs a portion of the fluorescent light 94 to light detector 29i. Changes in the amount of fluorescent light 94 reaching detector 29i are indicated by voltmeter 53i.

The amount of fluorescent light 94 which enters core 12i of element 11i from coating material 23i is dependent on the light transmissivity of that material. Thus if the coating material 23i is normally opaque as in this particular example, relatively little fluorescent light 94 is sensed by light detector 29i prior to absorption of fluid. Absorption of fluid increases the light transmissivity of coating material 23i and enables fluorescent light 94 to enter core 12i at a greater rate. This is detected by light detector 29i and indicated by voltmeter 53i.

An opaque cap 97 at the end 19i of fiber optic element 11i keeps ambient light from entering element 11i and thereby influencing the emission of fluorescent light 94 by coating material 23i. Light source 27i, lens 33i, beam splitter 96 and light detector 29i are disposed within an opaque housing 34i to keep such light away from the other end 16i of element 11i. A greater portion of the fluorescent light 94 is transmitted to the light detector 29i if cap 97 is a mirror but this also causes light 98 from source 27i to be directed back to the light detector. Dilution of the desired data by such light 98 from source 27i can be minimized by disposing a color filter 99 between beam splitter 96 and light detector 29i, the filter being one which selectively transmits the wavelength of the fluorescent light 94.

FIG. 10 depicts another fiber optic fluid monitor 24j that relies on still another optical effect to detect absorption of a fluid in an absorbent coating material 23j that exhibits changes of light transmissivity in response to such absorption. In particular, monitor 24j detects changes in light leakage between adjacent bundled fiber optic elements 11j and 101 that are induced by such absorption.

A light source 27j and focussing lens 33j are positioned to direct light into an end 16j of at least one fiber optic element 11j which has fluid absorbent coating material 23j of the hereinbefore described kind. An opaque cap 102 is disposed at the opposite end 19j of element 11j and is preferably a mirror in order to return light back along the element for repeated interactions with the coating material 23j. The other fiber optic elements 101 may have similar coating material 23j and similar caps 102 at one end. The opposite ends 103 of elements 101 are directed towards a light detector 29j which is preferably large enough to intercept all light that is emitted from ends 103. The other fiber optic elements 101 are disposed against element 11j, extend in parallel relationship with element 11j in this example and the coating materials 23j of the several fiber optic elements are fused together to form an integral fiber optic bundle 104.

Light leakage between adjacent fiber optic elements in a bundle is a phenomenum which is generally considered to be undesirable and efforts are made to minimize such leakage by selecting cladding materials and dimensioning the cladding with that objective in mind. In the present fluid detector 24j such leakage is minimal until the fluid to be detected is absorbed in the coating material 23j. Absorption of the fluid increases leakage of light from element 11j into elements 101. The leakage light then propagates along elements 101 and is sensed by light detector 29j thereby indicating the presence of the fluid in the region adjacent fiber optic elements 11j and 101.

While only two of the output fiber optic elements 101 have been depicted in FIG. 10, the input fiber optic element 11j may be surrounded by such elements 101 to increase sensitivity. Additional input fiber elements 11j may also be provided in the bundle 204. Detection of any of a plurality of different fluids may be arranged for by cladding individual ones of the fiber optic elements 101 with different coating materials 23j that are selectively absorptive of individual ones of the different fluids and by providing separate light detectors 29j at the end 103 of each such fiber optic element 101.

While the invention has been described with respect to certain specific embodiments and examples, many other variations and modifications are possible and it is not intended to limit the invention except as defined in the following claims.

I claim:

1. In fiber optic apparatus for detecting a predetermined fluid or any of a predetermined group of fluids, said apparatus having at least one fiber optic element which includes a light transmissive core and a coating thereon, a light source positioned to direct light into said fiber optic element for transmission therealong by repetitive internal reflections at the interface between said core and coating, and light detection means for detecting light which is emitted from said fiber optic element, the improvement comprising:

said fiber optic element being absorptive of said fluid or fluids, said coating along at least a portion of said core being a material which is absorptive of said fluid or fluids and which has an optical property that changes upon absorption of said fluid or fluids, and wherein said light detection means detects changes in a property of said emitted light that are caused by said changes of the optical property of the coating; and wherein said coating material has an index of refraction that changes upon absorption of said fluid or fluids and wherein said light is emitted from a first end of said fiber optic element, and wherein said light detection means includes a light detector spaced apart from said end of said fiber optic element, further including an opaque shield disposed between said first end and said light detector and having a configuration which blocks a portion of said emitted light from said detector.

2. The fiber optic apparatus of claim 1 wherein the light emitted from said first end of said fiber optic element diverges to define a cone of light and wherein said opaque shield has a light transmissive passage therethrough that has an area smaller than the area of said cone of light at the plane of said shield.

3. The fiber optic apparatus of claim 1 wherein the light emitted from said first end of said fiber optic element diverges to define a cone of light and wherein said opaque shield has an area smaller than the area of said cone of light at the plane of said shield.

4. In fiber optic apparatus for detecting a predetermined fluid or any of a predetermined group of fluids, said apparatus having at least one fiber optic element which includes a light transmissive core and a coating thereon, a light source positioned to direct light into said fiber optic element for transmission therealong by repetitive internal reflections at the interface between said core and coating, and light detection means for detecting light which is emitted from said fiber optic element, the improvement comprising:

said fiber optic element being absorptive of said fluid or fluids, said coating along at least a portion of said core being a material which his absorptive of said fluid or fluids and which has an optical property that changes upon absorption of said fluid or fluids, and wherein said light detection means detects changes in a property of said emitted light that are caused by said changes of the optical property of the coating; and wherein said light is emitted from a first end of said fiber optic element and diverges therefrom to define a cone of light having an axis which is coincident with the axis of said first end of said fiber optic element, and wherein said light detection means includes a light detector having a light sensitive region that is offset from said axis of said cone of light by a distance at least equal to the radius of said core of said fiber optic element.

5. In fiber optic apparatus for detecting a predetermined fluid or any of a predetermined group of fluids, said apparatus having at least one fiber optic element which includes a light transmissive core and a coating thereon, a light source positioned to direct light into said fiber optic element for transmission therealong by repetitive internal reflections at the interface between said core and coating, and light detection means for detecting light which is emitted from said fiber optic element, the improvement comprising:

said fiber optic element being absorptive of said fluid or fluids, said coating along at least a portion of said core being a material which is absorptive of said fluid or fluids and which has an optical property that changes upon absorption of said fluid or fluids, and wherein said light detection means detects changes in a property of said emitted light that are caused by said changes of the optical property of the coating; and an opaque housing having at least one fluid entry opening, and a light baffle positioned to inhibit entry of external light into said housing, and wherein at least a portion of said fiber optic element having said fluid absorptive coating material thereon is disposed within said housing.

6. In fiber optic apparatus for detecting a predetermined fluid or any of a predetermined groups of fluids, said apparatus having at least one fiber optic element which includes a light transmissive core and a coating thereon, a light source positioned to direct light into said fiber optic element for transmission therealong by repetitive internal reflections at the interface between said core and coating, and light detection means for detecting light which is emitted from said fiber optic element, the improvement comprising:

said fiber optic element being absorptive of said fluid or fluids, said coating along at least a portion of said core being a material which is absorptive of said fluid or fluids and which has an optical property that changes upon absorption of said fluid or fluids, and wherein said light detection means detects changes in a property of said emitted light that are caused by said changes of the optical property of the coating; and wherein said light detection means includes a first light detector producing a first output voltage that varies in accordance with variations in the amount of light received by the first light detector, further including an additional fiber optic element having a core with coating material thereon that does not absorb said fluid or fluids, means for directing a portion of the light from said light source into said additional fiber optic element, a second light detector positioned to receive light which is emitted from said additional fiber optic element and producing a second output voltage that varies in accordance with variations in the light received by the second light detector, means for producing a ratio signal that varies in accordance with variations of the ratio of said first and second output voltages, and means for indication changes in said ratio signal and wherein said means for directing a portion of the light from said light source into said additional fiber optic element directs substantially one half of said light into said additional fiber optic element, and wherein said fiber optic elements have substantially similar dimensions.

7. In fiber optic apparatus for detecting a predetermined fluid or any of a predetermined group of fluids, said apparatus having at least one fiber optic element which includes a light transmissive core and a coating thereon, a light source positioned to direct light into said fiber optic element for transmission therealong by repetitive internal reflections at the interface between said core and coating, and light detection means for detecting light which is emitted from said fiber optic element, the improvement comprising:

said fiber optic element being absorptive of said fluid or fluids, said coating along at least a portion of said core being a material which is absorptive of said fluid or fluids and which has an optical property that changes upon absorption of said fluid or fluids, and wherein said light detection means detects changes in a property of said emitted light that are caused by said changes of the optical property of the coating; and wherein said light source and said light detection means are both located at a first end of said fiber optic element, further including a mirror disposed at the opposite end of said fiber optic element, said mirror being oriented to return light back to said first end of said fiber optic element and wherein said mirror is spaced apart from said opposite end of said fiber optic element and is located to intercept and return only a portion of the light which is emitted from said opposite end.

8. In a fiber optic apparatus for detecting a predetermined fluid or any of a predetermined group of fluids, said apparatus having at least one fiber optic element which includes a light transmissive core and a coating thereon, a light source positioned to direct light into said fiber optic element for transmission therealong by repetitive internal reflections at the interface between said core and coating, and light detection means for detecting light which is emitted from said fiber optic element, the improvement comprising:

said fiber optic element being absorptive of said fluid or fluids, said coating along at least a portion of said core being a material which is absorptive of said fluid or fluids and which has an optical property that changes upon absorption of said fluid or fluids, and wherein said light detection means detects changes in a property of said emitted light that are caused by said changes of the optical property of the coating; and wherein said light source and said light detection means are located at a first end of said fiber optic element and said light is transmitted to the opposite end thereof, further including a return fiber optic element with a first end positioned to receive light from said opposite end of said fiber optic element and with a second end at the first end of the fiber optic element positioned to transmit said light back to said light detection means and wherein said absorptive coating material is on a portion of said core that is remote from said light source and light detection means and wherein portions of said core that are closer to said light source and light detection means are coated with non-absorptive coating material, said return fiber optic element also having a coating of non-absorptive coating material.

9. In fiber optic apparatus for detecting a predetermined fluid or any of a predetermined group of fluids, said apparatus having at least one fiber optic element which includes a light transmissive core and a coating thereon, a light source positioned to direct light into said fiber optic element for transmission therealong by repetitive internal reflections at the interface between said core and coating, and light detection means for detecting light which is emitted from said fiber optic element, the improvement comprising:

said fiber optic element being absorptive of said fluid or fluids, said coating along at least a portion of said core being a material which is absorptive of said fluid or fluids and which has an optical property that changes upon absorption of said fluid or fluids, and wherein said light detection means detects changes in a property of said emitted light that are caused by said changes of the optical property of the coating; and wherein said light source and said light detection means are located at a first end of said fiber optic element and said light is transmitted to the opposite end thereof, further including a return fiber optic element with a first end positioned to receive light from said opposite end of said fiber optic element and with a second end at the first end of the fiber optic element positioned to transmit said light back to said light detection means and wherein the light emitted from said opposite end diverges therefrom to define a cone of light, and wherein the light input end of said return fiber optic element is spaced apart from said opposite end and intercepts only a portion of said cone of light.

10. In fiber optic apparatus for detecting a predetermined fluid or any of a predetermined group of fluids, said apparatus having at least one fiber optic element which includes a light transmissive core and a coating thereon, a light source positioned to direct light into said fiber optic element for transmission therealong by repetitive internal reflections at the interface between said core and coating, and light detecting means for detecting light which is emitted from said fiber optic element, the improvement comprising:

said fiber optic element being absorptive of said fluid or fluids, said coating along at least a portion of said core being a material which is absorptive of said fluid or fluids and which has an optical property that changes upon absorption of said fluid or fluids, and wherein said light detection means detects changes in a property of said emitted light that are caused by said changes of the optical property of the coating; and wherein said coating material is a material which produces fluorescent light in response to light from said light source and which exhibits a change light transmissivity in response to absorption of said fluid or fluids, and wherein said light detection means detects said fluorescent light.

11. The fiber optic apparatus of claim 10 wherein said light source is positioned to direct light into a first end of said fiber optic element, further including an opaque end cap disposed at the opposite end of said fiber optic element, and means for directing fluorescent light that is emitted from said first end of said fiber optic element to said light detection means.

12. The fiber optic apparatus of claim 10 wherein said coating material is a polymeric substance impregnated with a fluorescent organic dye.

13. In fiber optic apparatus for detecting a predetermined fluid or any of a predetermined group of fluids, said apparatus having at least one fiber optic element which includes a light transmissive core and a coating thereon, a light source positioned to direct light into said fiber optic element for transmission therealong by repetitive internal reflections at the interface between said core and coating, and light detection means for detecting light which is emitted from said fiber optic element, the improvement comprising:

said fiber optic element being absorptive of said fluid or fluids, said coating along at least a portion of said core being a material which is absorptive of said fluid or fluids and which has an optical property that changes upon absorption of said fluid or fluids, and wherein said light detection means detects changes in a property of said emitted light that are caused by said changes of the optical property of the coating; and wherein said coating material on said fluid absorbent fiber optic element is a material which exhibits changes of light transmissivity in response to absorption of said fluid or fluids, further including at least one additional fiber optic element disposed against said coating material, and wherein said light detection means detects light which leaks into said additional fiber optic element through said coating material.

14. The fiber optic apparatus of claim 13 wherein said fluid absorbent fiber optic element and said additional fiber optic element each have first and second ends, said light source being positioned to direct light into said first end of said fluid absorbent fiber optic element and wherein said light detection means detects light emitted from said first end of said additonal fiber optic element, further including first and second opaque end caps disposed at said second ends of fluid absorbent fiber optic element and said additional fiber optic element respectively.

15. The fiber optic apparatus of claim 14 wherein each of said end caps is a mirror.

16. The fiber optic apparatus of claim 13 wherein at least a portion of said additonal fiber optic element has said fluid absorptive coating material thereon and wherein said coating materials of said fluid absorbent fiber optic element and said additional fiber optic element are fused together.

* * * * *